(12) United States Patent
Song

(10) Patent No.: US 7,970,178 B2
(45) Date of Patent: Jun. 28, 2011

(54) VISIBILITY RANGE ESTIMATION METHOD AND SYSTEM

(75) Inventor: Guobiao Song, Memphis, TN (US)

(73) Assignee: Caterpillar Inc., Peoria, IL (US)

( * ) Notice: Subject to any disclaimer, the term of this patent is extended or adjusted under 35 U.S.C. 154(b) by 856 days.

(21) Appl. No.: 11/962,098

(22) Filed: Dec. 21, 2007

(65) Prior Publication Data

US 2009/0161914 A1   Jun. 25, 2009

(51) Int. Cl.
  *G06K 9/00* (2006.01)
(52) U.S. Cl. ........ 382/106; 382/103; 382/105; 382/107; 356/437; 356/342
(58) Field of Classification Search .............. 382/105, 382/106, 103, 107; 356/437, 5.01, 342, 5.08; 348/97, 154, 155, 239, 460, 471, 699, 700; 375/240.01, 240.16, 240.26
See application file for complete search history.

(56) References Cited

U.S. PATENT DOCUMENTS

| | | | |
|---|---|---|---|
| 5,719,773 A | 2/1998 | Choate | |
| 5,914,776 A * | 6/1999 | Streicher | 356/5.01 |
| 6,330,858 B1 | 12/2001 | McDonough et al. | |
| 6,429,789 B1 | 8/2002 | Kiridena et al. | |
| 6,446,692 B1 | 9/2002 | Sugiyama | |
| 6,449,384 B2 | 9/2002 | Laumeyer et al. | |
| 6,463,181 B2 | 10/2002 | Duarte | |
| 6,760,024 B1 * | 7/2004 | Lokovic et al. | 345/421 |
| 6,853,453 B2 * | 2/2005 | Kwon | 356/437 |
| 6,898,331 B2 | 5/2005 | Tiana | |
| 6,947,576 B2 | 9/2005 | Stam et al. | |
| 7,016,045 B2 * | 3/2006 | Kwon | 356/437 |
| 7,072,523 B2 | 7/2006 | Bolle et al. | |
| 7,142,723 B2 | 11/2006 | Kang et al. | |
| 7,191,056 B2 | 3/2007 | Costello et al. | |
| 7,646,890 B2 * | 1/2010 | Kobayashi et al. | 382/106 |
| 7,796,081 B2 * | 9/2010 | Breed | 342/70 |
| 2005/0013486 A1 | 1/2005 | Wiedemann et al. | |
| 2006/0088191 A1 | 4/2006 | Zhang et al. | |
| 2006/0153459 A1 | 7/2006 | Zhang et al. | |
| 2006/0245618 A1 | 11/2006 | Boregowda et al. | |
| 2006/0245653 A1 | 11/2006 | Camus et al. | |

OTHER PUBLICATIONS

Nicolas Hautiere, Jean-Philippe Tare, Jean Lavenant and Didier Aubert, "Automatic fog detection and estimation of visibility distance through use of an onboard camera," Machine Vision and Applications (2006) 17(1):8-20, DOI 10.1007/s00138-006-001.1-9, Jan. 27, 2006, pp. 8-20.
Christoph Busch and Eric Debes, "Wavelet Transform for Analyzing Fog Visibility," IEEE Intelligent Systems, Nov./Dec. 1998, pp. 66-71.

* cited by examiner

*Primary Examiner* — Daniel G Mariam
*Assistant Examiner* — Nancy Bitar
(74) *Attorney, Agent, or Firm* — Joanna Xuqiong Wu

(57) ABSTRACT

The present disclosure provides methods and systems for estimating a visibility range in a visibility-degraded environment, e.g., fog. The methods and systems involve digital image processing.

20 Claims, 10 Drawing Sheets

(OFF-HIGHWAY)

(ON-HIGHWAY)

CONTRAST ATTENUATION

Exponential Attenuation: $C = C_0 \cdot e^{-\gamma d}$
$C_0$: Original contrast
$C$: Current contrast at distance $d$
$\gamma$: Attenuation factor

DILATED CONTRAST IMAGE

CONTRAST MAP INSIDE THE ROI

BINARY CONTRAST MAP GENERATED BY THE ADVANCED ALGORITHM

BINARY CONTRAST MAP GENERATED BY THE SIMPLE ALGORITHM

BINARY CONTRAST MAP GENERATED
BY THE ADVANCED ALGORITHM

BINARY CONTRAST MAP GENERATED
BY THE SIMPLE ALGORITHM

VISIBILITY RANGE ESTIMATION METHOD AND SYSTEM

TECHNICAL FIELD

This disclosure relates, generally, to the field of control and communication systems and methods, and more particularly, to systems and methods for estimating visibility range.

BACKGROUND

To increase machine and operator safety, particularly in poor visibility conditions, special sensors such as cameras, laser, and radar have been introduced to certain vehicles, for either on-highway or off-highway applications. An example of the sensor systems is one capable of detecting the presence of a visibility-degraded condition, such as for example, fog, and estimating visibility ranges.

This sensor system can function as a driving aid. For example, in fog, humans, based on naked eyesight alone, tend to overestimate visibility ranges (see Cavallo et al., *Hum. Factors* 43: 442-451 (2001)), which may lead to excessive driving speeds or other risky driving maneuvers. A sensor system that provides a more accurate visibility range estimation in real time would serve to inform the vehicle operator of visibility degradation and could further include a control strategy to restrict the speed or other potentially risky driving maneuvers based on the detected or estimated condition.

Busch and Debes, *IEEE Intelligent Sys.*, November/December 1998, 66-71, described a method based on a B-spline wavelet transform for analyzing video frames used in traffic-control systems and deriving a visibility range measure with extended signal-analysis techniques. Their system can be used to inform vehicle operators in real time of the presence of fog through VMS located at a distance away from the foggy area. However, this system relies on a fixed or static camera, not suitable for on-board applications on a moving vehicle. Further, the use of a single camera does not allow direct measurement of image depth. Thus, the Busch and Debes method also includes selecting a Region of Interest (ROI) in the digital images obtained by the fixed camera and assuming that all the pixels inside the ROI lie in one plane (e.g., a flat road) so as to conduct an inverse geometric transform. Busch and Debes' use of a video sequence may also be problematic, because from frame to frame certain undesired objects can vary greatly, making the selection of the ROI difficult.

Hautière et al., *Machine Vision and Applications*, 17(1): 8-20 (2006), reported a fog-detection and visibility-estimation system using an on-board camera. This system uses a preprocessing procedure by means of region growing, which allows for the determination of the most pertinent objects or pixels in the images obtained by the on-board camera. The most pertinent objects are then analyzed with a computation model based on Koschmieder's model and Duntley's attenuation law of atmospheric contrasts. Similarly, this single-camera system does not provide direct measurement of image depth, and therefore, the Hautière et al. approach also adopts the hypothesis of a flat road.

However, road conditions can vary greatly, particularly in off-highway applications. Thus, there remains a need for a more robust and accurate method for estimating visibility range in real time under a variety of circumstances, such as for example on-board use on vehicles for either on-highway or off-highway applications or both, or on-board use on other vessels or equipment, wherever a need for real-time estimation of visibility range exists.

The present disclosure is directed to addressing this need and other problems described above.

SUMMARY

In one aspect, this disclosure provides a method for estimating a visibility range of an area. The method includes obtaining a digital image of at least a portion of the area. The method further includes selecting a first region of interest from the digital image and obtaining a contrast map and a distance map of the first region of interest. The method also includes calculating a visibility attenuation factor based on the contrast map and the distance map of the first region of interest. The method may include selecting a second region of interest from the digital image and further selecting pixels in the second region of interest based on the visibility attenuation factor. The method also includes finding a pixel representing the longest distance having a contrast at or above 5%, and the distance of that pixel can then be utilized to determine the visibility range.

In another aspect, this disclosure provides a system for estimating a visibility range of an area. The system includes a processor configured to obtain a contrast map and a distance map for a first region of interest in a digital image of at least a portion of the area and calculate a visibility attenuation factor based on the contrast and distance maps. The processor is further configured to select pixels from a second region of interest in the digital image based on the visibility attenuation factor. The processor is also configured to find a pixel representing the longest distance having a contrast at or above 5%.

DETAILED DESCRIPTION

Figure 1:
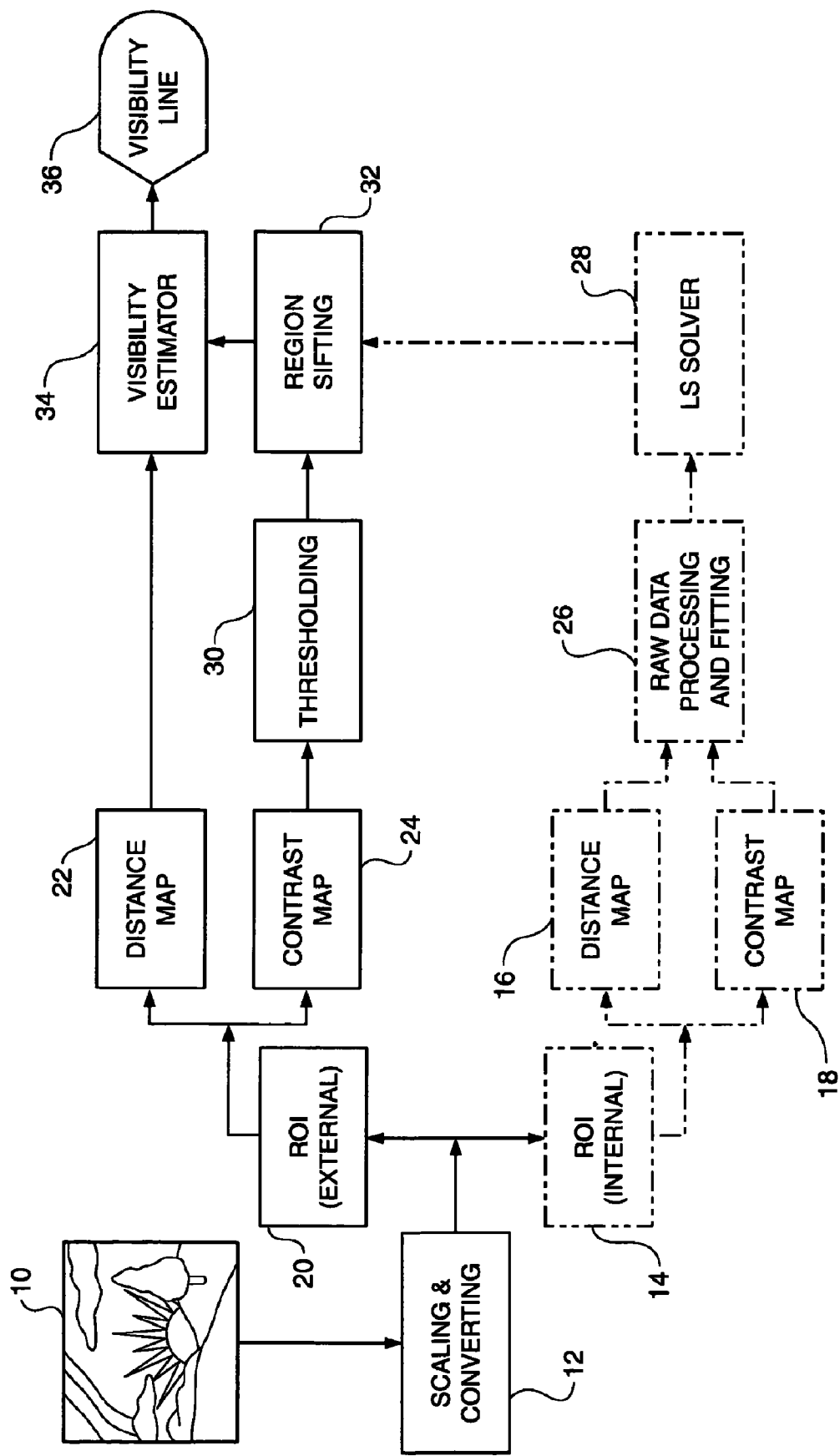
FIG. 1 is a flow diagram illustrating the processing of a digital image to estimate visibility range as indicated by a visibility line.
Figure 3:
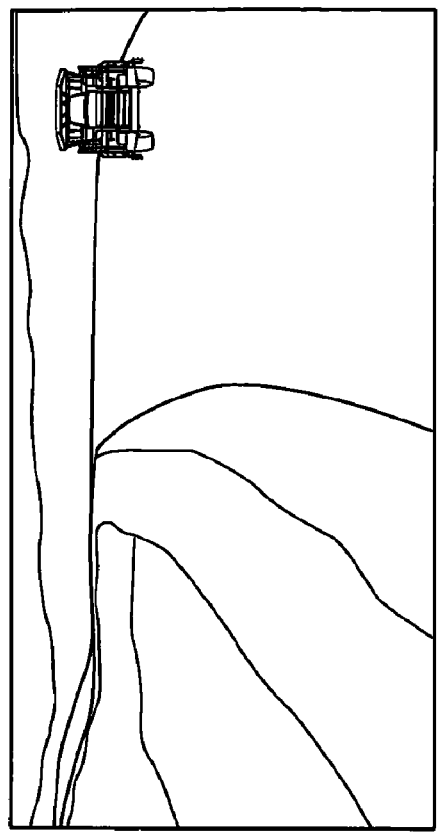
FIG. 2 and FIG. 3 compare on-highway and off-highway images to illustrate the difficulty in selecting an ROI in an off-highway application.

In certain embodiments, for example as represented by the flow diagram in FIG. 1, the method includes obtaining a digital image 10 using a digital imaging device, e.g., a digital camera (not shown). The digital imaging device may be on board of a mobile vehicle or machine, such as for example, an on-highway vehicle, an off-highway truck, a dozer, a wheel loader, an excavator, etc., which can be part of the safety or security system of the mobile vehicle or machine. The digital imaging device can be switched on and off manually or automatically as desired or alternatively stay on continuously, particularly during operation of the mobile vehicle or machine. The digital image 10 is then scaled and converted for further processing, as shown in block 12.

The method as illustrated in FIG. 1 also includes selecting a first or internal ROI, as shown in block 14. Blocks 16 and 18 represent the steps of calculating, respectively, a distance map and a contrast map for the internal ROI. Further, block 20 represents the step of selecting a second or external ROI, to be further processed before the visibility estimation algorithm is applied. Similarly, a distance map and a contrast map for the external ROI are calculated, according to blocks 22 and 24, respectively.

The first and second ROIs can be selected manually or automatically based on one or more predefined criteria. For example, the ROIs may be selected from the part of the digital image showing the center area in front of the digital camera, or the ROIs may be selected from the part of the digital image that does not have extruding or large objects such as trees, houses, or other apparent road obstacles.

Figure 2:
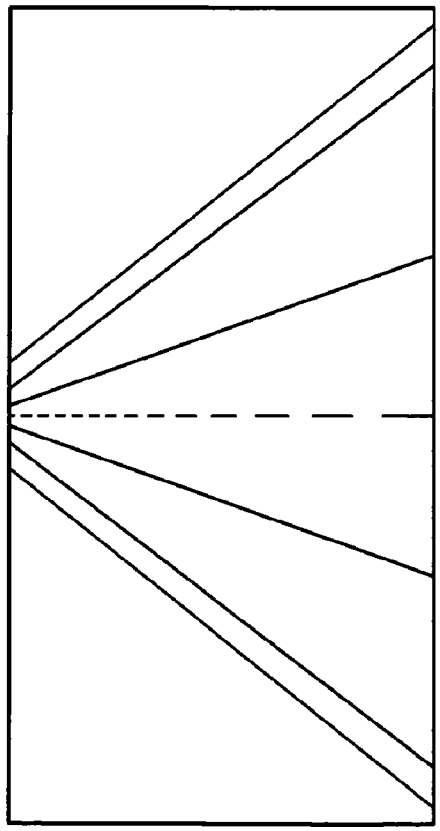

FIG. 2A shows an ROI selected from a digital image obtained in an on-highway application, which ROI can be the area right in front of the digital camera along the straight road. FIG. 2B shows a digital image of an off-highway environment, which indicates the difficulty in selecting an ROI due to the road curves and obstacles.

A contrast map can be calculated based on the intensity profile of each pixel of the internal ROI. The contrast map can be obtained by different methods such as for example, two ways known in the art as follows:

1) Direct calculation. The contrast is usually defined as:

$$C = \frac{|I_0 - I_b|}{I_0 + I_b},$$

where $I_0$ is the object's intensity and $I_b$ is the background's intensity. In a digital image, the contrast is often calculated in a small neighborhood of each pixel. The neighborhood is typically a rectangle in order to simplify calculation and should be small enough. Inside the neighborhood, the contrast is given by:

$$C = \frac{|I_{max} - I_{min}|}{I_{max} + I_{min}}.$$

2) B-spline wavelet transform, as reported by Busch and Debes. Visual perception is a rather complex mechanism based on space, time and frequency analyses. Human retina's response often resembles a Gaussian function. B-splines are used to approximate the human psychovisual perception, because their Fourier transforms and themselves converge to the Gaussian functions as the order of the spline extends to infinity. Thus the wavelet transform based on B-splines can be well suited to estimate gradients (or contrast) in an image in a similar way to human eyes.

A distance map can be obtained based on the camera configuration, which is used to conduct the inverse geometric transform from the image coordinates to world coordinates. Essentially the projection from the world coordinate system to the image coordinate system is a three-dimension to two-dimension mapping. In order to obtain the inverse mapping, the assumption that the pixels within an ROI all lie in a single or the ground plane is usually necessary. Therefore, to ensure accuracy or reduce errors, it is desirable to select only the pixels that satisfy this assumption for further processing including the inverse geometric transform.

A distance computation model is described by Hautière et al. This report also estimated distance calculation accuracy versus the camera pitch angle. At a smaller pitch angle, the resulting digital image usually has a raised horizon line, which leads to decreased surface area covered by a pixel and increased accuracy in distance calculation.

Figure 4:
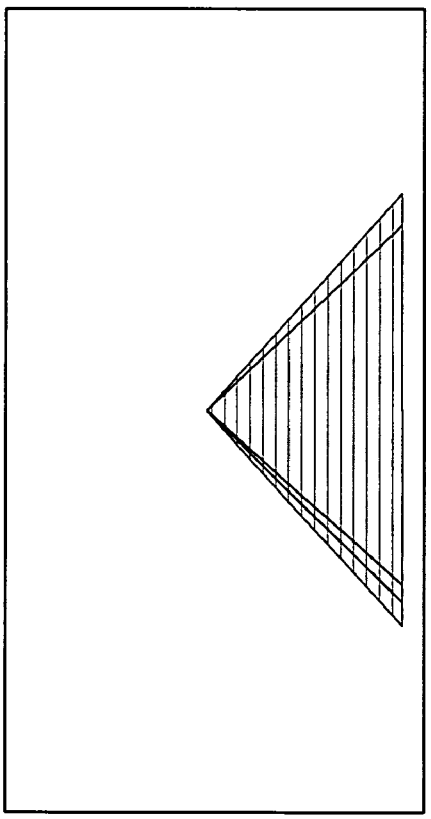

Referring back to FIG. 1, block 26 represents the step of raw data processing and fitting based on the distance map and the contrast map of the internal ROI. To illustrate this step, FIGS. 4 and 5, respectively, show an example of internal ROI and external ROIs of a digital image. The internal ROI in FIG. 4 includes lines at varying distances away from the digital camera.

Figure 6:
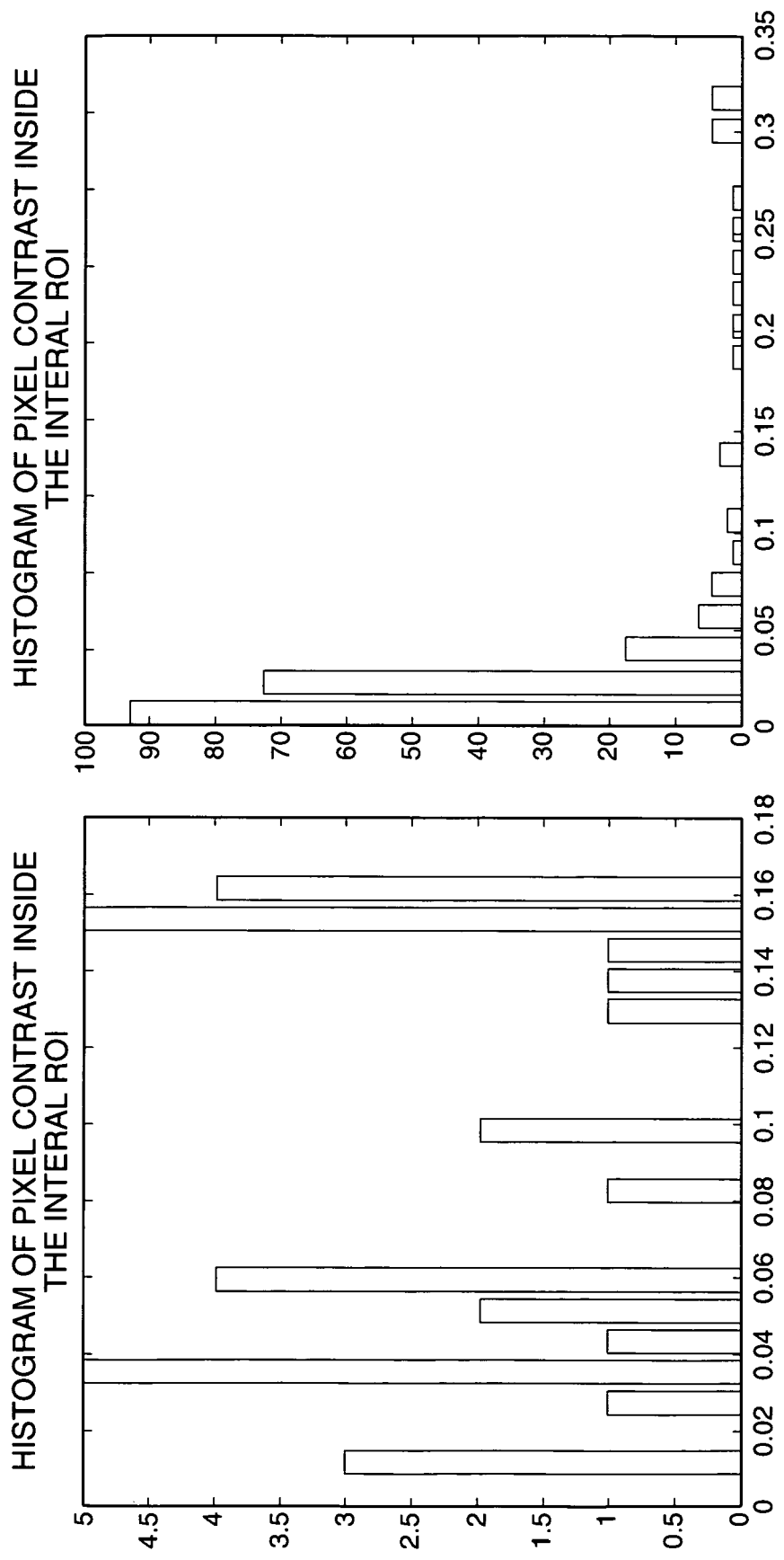
FIG. 6 shows a typical contrast histogram of image pixels in a region close to the camera versus a typical contrast histogram of image pixels in a region further away from the camera.
Figure 7:
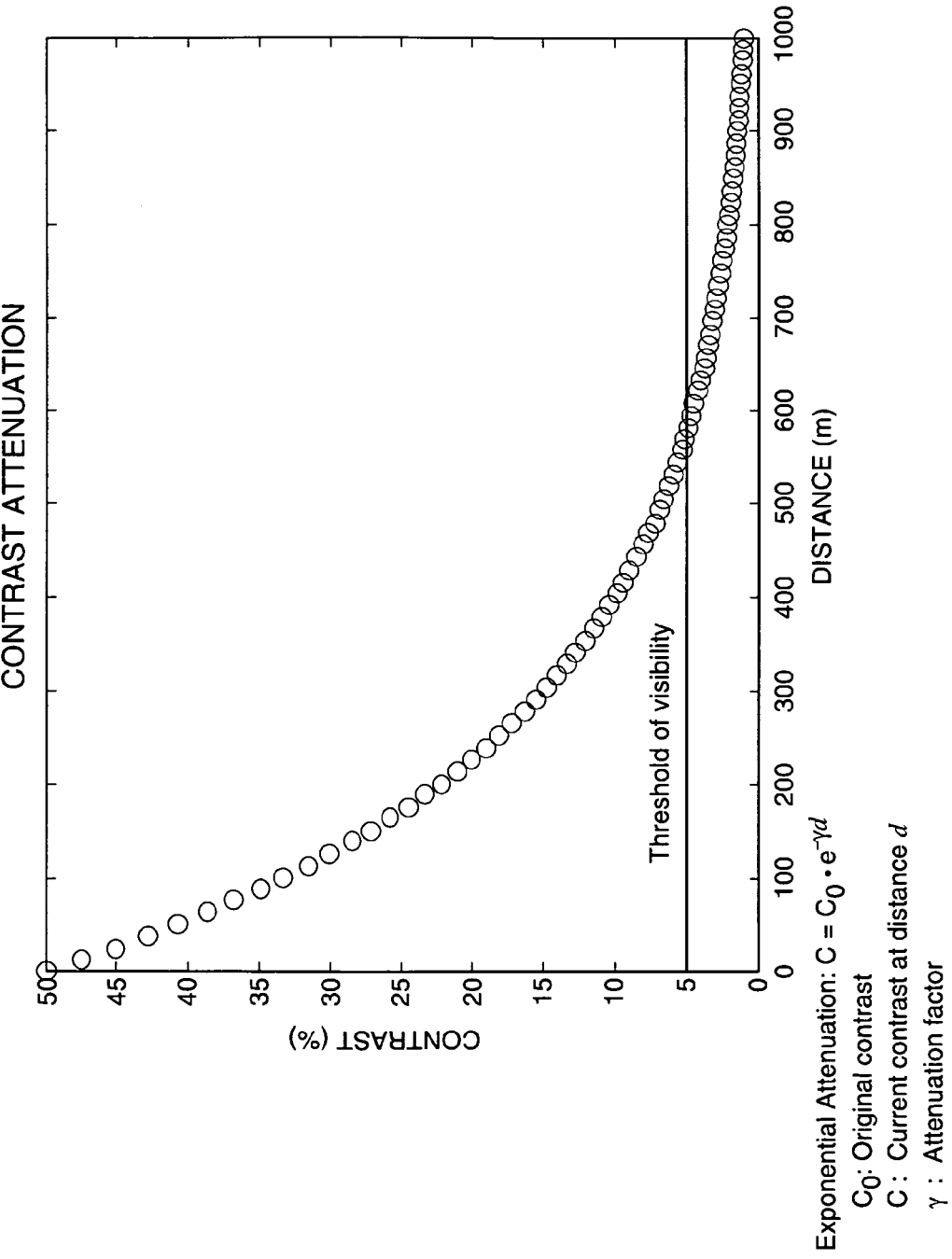
FIG. 7 illustrates a typical contrast attenuation model in fog.

FIG. 6 compares a typical contrast histogram of pixels in a region close to the camera against a typical contrast histogram of pixels in a region far away from the camera. As expected, the contrasts of pixels in close range provide a stable inverse correlation distribution with respect to the distances of the pixels. In contrast, the contrast histogram of pixels in distance shows a random distribution, which is likely due to inclusion of undesirable features or objects on the digital image at a distance. It is reasonable to assume that the contrast histogram of pixels should follow a typical contrast attenuation model, such as for example as shown in FIG. 7, where the attenuation of contrasts of objects (i.e., visibility degradation) obeys an exponential law:

$$C = C_0 e^{-\gamma \cdot d}$$

where $C_0$ is the original contrast of the object, $\gamma$ is the attenuation factor, d is the distance of the object and C is the contrast at distance d, as formulated by Duntley in 1948. Accordingly, one criterion for selecting an internal ROI can be that pixels in the internal ROI at difference distances from the camera having similar contrast histograms. In certain embodiments, a pixel in the internal ROI having a contrast that deviates from the typical contrast histogram showing an inverse correlation between contrast and distance is removed from further processing.

Figure 8:
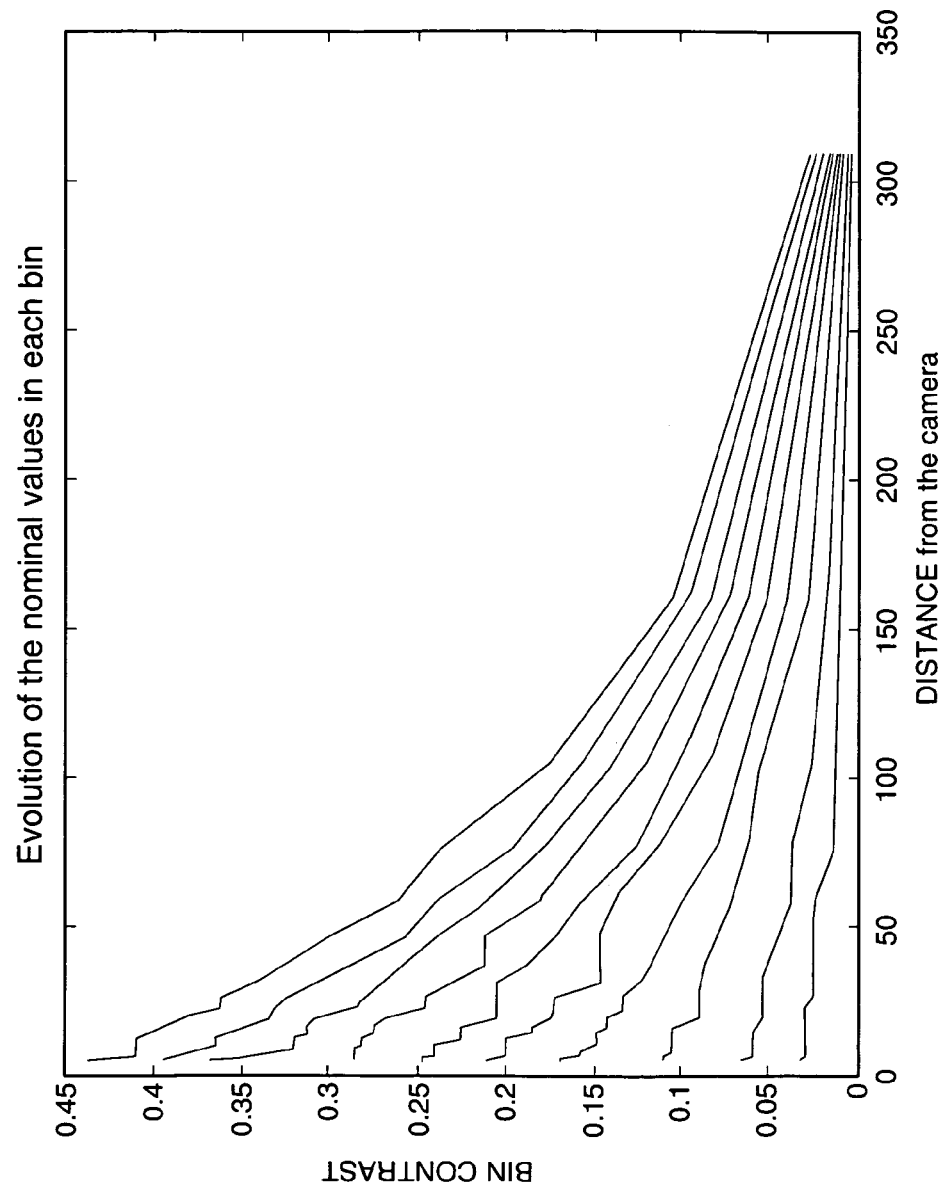
FIG. 8 illustrates contrasts with respect to distances for 10 bins of pixels.
Figure 9:
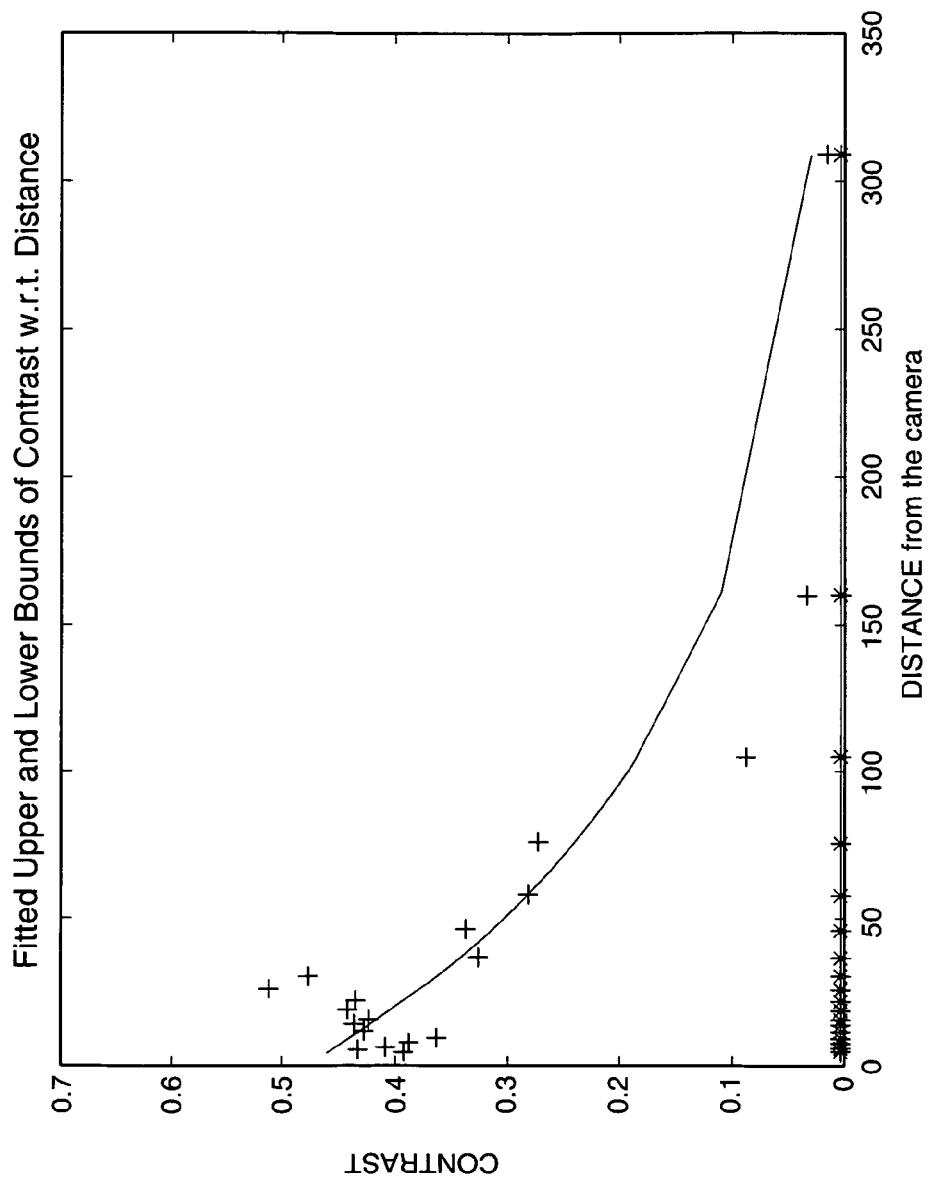
FIG. 9 illustrates the estimation of an attenuation model based on the 10 bins of pixels as shown in FIG. 8.
Figure 10:
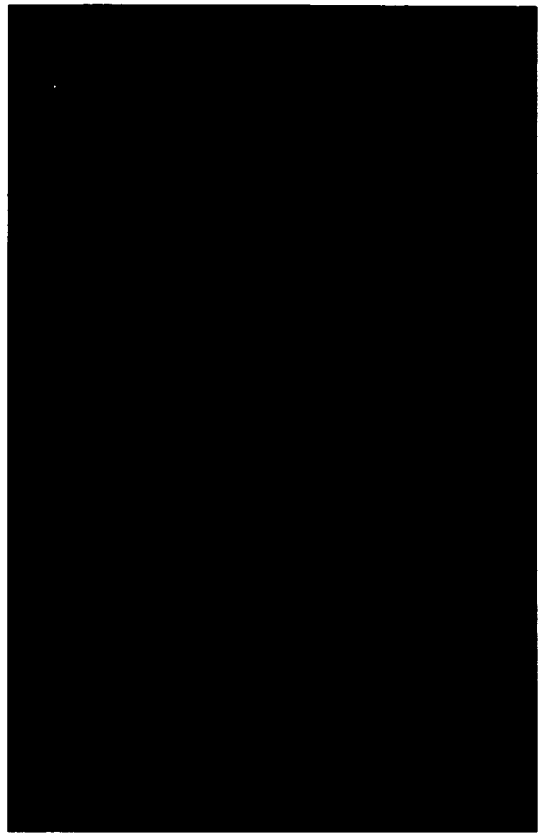
FIG. 10 illustrates the data sifting for pixels in the external or second ROI (left panel: contrast map before sifting; right panel: contrast map after sifting).
Figure 10:
Figure 11:
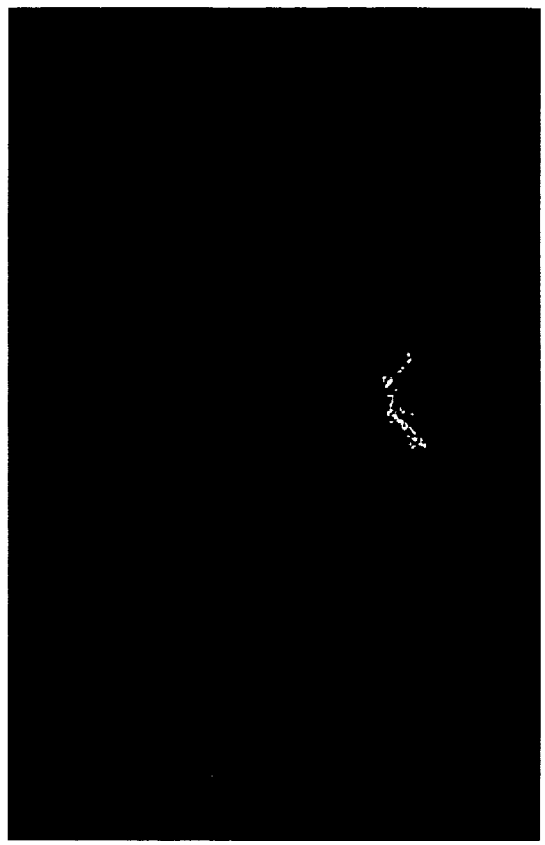
FIG. 11 compares the contrast map for an ROI using an existing method (simple algorithm) and the contrast map for an ROI using a method of the present disclosure (advanced or improved algorithm).
Figure 11:

FIG. 8 further illustrates the data fitting following the raw data processing as described above. The remaining pixels in the internal ROI with a desirable contrast histogram are grouped into N bins (e.g., N=10), representing N rows of pixels, as shown in FIG. 8. Subsequently, the centers of the N bins are calculated, and the upper and lower boundaries of the contrasts for these N bins of pixels are then fitted with respect to distance, as shown in FIG. 9. The Least Square method is then applied to the fitted curve to solve the attenuation factor $\gamma$, as represented by block 28 of FIG. 1.

The method as shown in FIG. 1 also includes the step of thresholding, as represented by block 30. CIE (International Commission of Lighting) defined a 5% contrast threshold for a human eye to see the difference between two gray levels, i.e., visible to a human eye. Accordingly, the step of thresholding includes removing from further processing those pixels having a contrast (as calculated by contrast mapping) below this 5% threshold.

Further sifting of pixels of the external ROI after the thresholding in block 30 is performed in block 32, taking in account the attenuation factor γ, obtained from block 28. For example, the exponential model described above with the attenuation factor γ obtained from block 28 can be used to calculate contrasts at the pixels passing the 5% threshold contrast. The calculated contrasts can then be compared against the contrast map obtained from block 24, and only pixels with comparable calculated contrasts and mapped contrasts are retained for further processing.

The visibility estimation algorithm is then applied to the sifted and retained pixels from block 32 in view of the distance map obtained from block 22. The pixel(s) with the furthest distance then forms the visibility line in block 36, which distance represents the estimated visibility range.

In certain aspects, a method of the present disclosure may further include communicating the estimated visibility range to the operator of the mobile vehicle or machine, for example, through a user interface.

In certain aspects, the estimated visibility range is shown as a visibility line on a user interface.

In certain aspects, a method of the present disclosure may also include communicating the estimated visibility range to one or more control systems of the mobile vehicle or machine, such as for example the engine ECM, which may then lead to reduced speed or inability to operate the vehicle or machine in certain ways (e.g., risky maneuvers such as sudden turns or backing up).

In certain aspects, a method of the present disclosure is applied to detect the presence of a visibility-degraded condition. For example, according to Busch and Debes, the German federal traffic department defines a visibility distance over 1000 m as "no fog." Accordingly, a step of comparing the estimated visibility range with a pre-defined value, e.g., 1000 m, can be included in the method, and the method may further include communicating the result, e.g., "no fog" or "fog," optionally with the estimated visibility range, to the operator.

Another aspect of the present disclosure provides a visibility range estimation system, such as for example a system employing the method as illustrated in FIG. 1 and described above. The system may be physically separate but operably linked to a digital camera or include a digital camera. The system may also include one or more computational devices for processing images obtained by the digital camera. The system may further include a user interface such as for example a computer monitor.

A further aspect of the present disclosure provides a computer-readable medium with embedded codes for carrying out one or more steps of a method described herein, such as for example, the steps as represented by blocks 12, 14, 16, 18, 20, 22, 24, 26, 28, 30, 32, 34, and 36 in FIG. 1.

INDUSTRIAL APPLICABILITY

One aspect of the disclosure provides a method for estimating visibility distance or range. The method may involve the use of a digital camera, which may be on board of a mobile vehicle, machine, vessel, or other equipment. The method includes selecting a region of interest (ROI) inside a digital image, e.g., an image obtained by a digital camera. The method further includes calculating a contrast map of the ROI. In certain embodiments, the method also includes removing unwanted features (and pixels) in the ROI. The method also includes calculating parameter estimation, which can be based on different methods depending on the applicable visibility attenuation models. For example, the Least Square method is suitable for the visibility attenuation model in fog, according to an illustrated embodiment of the present disclosure. Further, the method includes sifting data obtained from the ROI, which leaves only valid pixels for final processing. Finally, the method includes transforming coordinates from the image plane to world coordinate system.

In certain alternative embodiments, the method may include searching for an appropriate ROI in the digital image, instead of selecting an ROI and then removing undesirable features in the selected ROI, before further processing by applying the visibility range estimation algorithm. Searching for the appropriate ROI may include utilizing computational methods known to those in the art.

Figure 5:
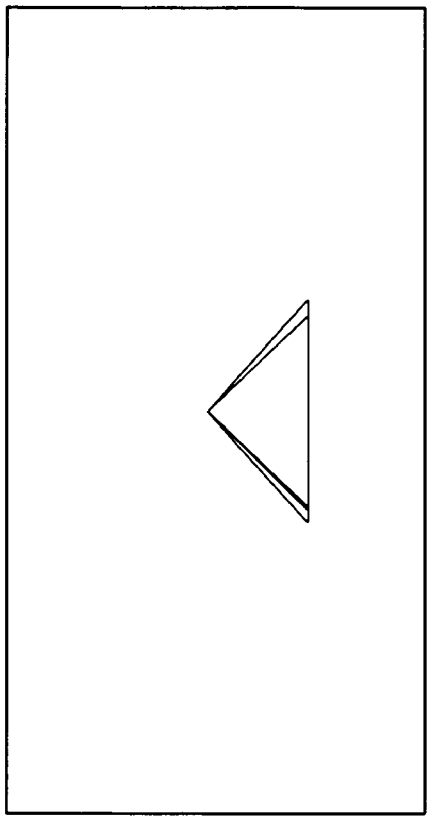
FIG. 4 and FIG. 5, respectively, show examples of a first or internal ROI and a second or external ROI selected from a digital image.

The visibility estimation systems and methods described herein are suitable for various applications, including but not limited to on-board use on off-highway as well as on-highway vehicles, or addressing a need for real-time estimation of visibility range in a visibility-degraded environment. Although the attenuation model described herein, such as for example as shown in FIG. 5 is particularly suitable for fog, the systems and methods can be adapted to be based on attenuation models suitable for other visibility-degraded environments, such as adverse weather (e.g., rain or snow) or poor lighting (e.g., night) conditions.

An exemplary visibility range estimation method and system using the algorithm as depicted in FIG. 1 (improved algorithm) was tested in various applications and compared against an existing algorithm (simple algorithm). In these applications, the estimated visibility range is shown (as visibility range) on a computer monitor, i.e., a user interface. Further, in each of these examples, the visibility range estimated using an existing method (i.e., simple algorithm) is compared against the visibility range estimated using the exemplary method of the present disclosure (i.e., improved algorithm). The existing method using the simple algorithm essentially is as reported by Busch and Debes, which includes the steps as represented by blocks 10, 12, 20, 22, 24, 30, 34, and 36 of FIG. 1, but does not include the steps associated with the internal ROI selection and processing.

In a first test on a straight, flat part of a road, the visibility ranges estimated by the improved algorithm and the simple algorithm are similar and at 110.0167 meters and 116.6055 meters, respectively. However, the result based on the simple algorithm depends greatly on the selection of ROI: in a test on the same straight, flat part of the road, where the ROI was manually selected, the simple algorithm resulted in an estimated visibility range of 274.038 meters; in contrast, the improved algorithm resulted in an estimated visibility range of 113.8283 meters similar to the result based on automatically selected ROI shown above.

Figure 12:
FIG. 12 shows an example of a comparison of binary contrast maps based on an existing method (simple algorithm) and a method of the present disclosure (improved algorithm) of an image taken at nighttime on a highway. The oval in the contrast map on the left was added artificially to indicate the high contrasts created by a vehicle's headlights as captured in the digital image used for this analysis. Accordingly, results obtained by the simple algorithm can be inaccurate due to its susceptibility to various factors or features.
Figure 12:
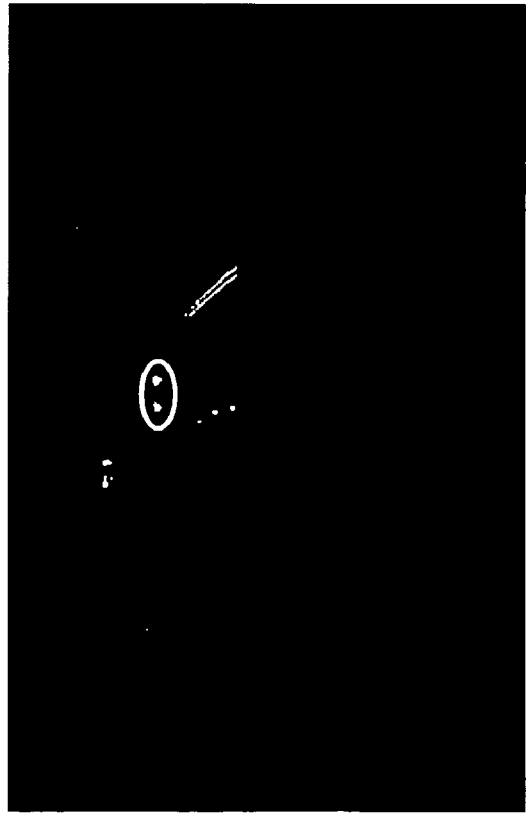

Further, curved road, night light (e.g., FIG. 12), non-uniform and unpredictable background in an off-highway construction site all greatly affect the results obtained by the simple algorithm. For example, in another test on a curved part of the same road as in the first test, the improved algorithm resulted in an estimated visibility range of 130.1271 meters; in contrast, the simple algorithm resulted in an estimated visibility range of 1969.2424 meters, which may give a "no fog" result. Another test was run at night, and as shown in FIG. 12, the presence of other vehicle headlights could greatly affect the binary contrast map obtained by the simple algorithm.

In a further off-highway test, when the ROI is predefined, the improved algorithm resulted in an estimated visibility range of 366.6671 meters, whereas the simple algorithm resulted in an estimated visibility range of 992.5676 meters. Under the same off-highway condition, when the ROI is manually selected, the improved algorithm resulted in an estimated visibility range of 373.1726 meters, compared to that obtained with a predefined ROI; in contrast, the simple algorithm resulted in an estimated visibility range of 2146.2369 meters.

Accordingly, the improved algorithm or the exemplary method (and system) of the present disclosure provides a robust and accurate estimation of visibility range and is useful in various applications under varying conditions.

It will be apparent to those skilled in the art that various modifications and variations can be made to the disclosed paving machine output monitoring system without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims and their equivalents.

All references cited herein are incorporated by reference in their entirety.

What is claimed is:

1. A method for determining a visibility range of an area, comprising:
    obtaining at least one digital image of at least a portion of the area;
    selecting a first region of interest from the at least one digital image and calculating a visibility attenuation factor based on a contrast map and a distance map of the first region of interest;
    selecting a second region of interest from the at least one digital image and selecting pixels in the second region of interest based on the visibility attenuation factor; and
    finding a pixel representing the longest distance and having a contrast around or above 5%,
    wherein the visibility range is determined based on the distance of the pixel.

2. The method of claim 1, wherein the digital image is obtained using a digital imaging device.

3. The method of claim 2, wherein the digital imaging device is on board of a vehicle or machine.

4. The method of claim 1, wherein the area has a substantially uniform visibility degradation.

5. The method of claim 4, wherein the visibility degradation substantially follows an exponential decrease of contrast with respect to distance of pixels.

6. The method of claim 5, wherein calculating the visibility attenuation factor includes applying a Least Square method.

7. The method of claim 1, wherein selecting a first image region and calculating the visibility attenuation factor include:
    obtaining a contrast map and a distance map for a plurality of pixels in the first region of interest;
    obtaining a contrast histogram of a plurality of pixels at more than one distance from the digital camera,
    and selecting a plurality of bins of pixels having similar contrast histogram profiles.

8. The method of claim 1 further including communicating the determined visibility range through a user interface.

9. The method of claim 8 further including indicating the determined visibility range with a visibility line on the user interface.

10. The method of claim 1, wherein the first and second regions of interest are manually or automatically selected from the digital image.

11. A system for determining a visibility range of an area, comprising:
    a processor configured to
        obtain a contrast map and a distance map for a first region of interest of a digital image of at least a portion of the area;
        calculate a visibility attenuation factor based on the contrast map and the distance map of the first region of interest;
        select pixels from a second region of interest of the digital image based on the visibility attenuation factor; and
        find a pixel representing the longest distance and having a contrast around or above 5%.

12. The system of claim 11, wherein the processor is configured to communicate the distance of the pixel representing the longest distance and having a contrast at or above 5% to an operator.

13. The system of claim 12, wherein the processor is configured to convert the distance of the pixel representing the longest distance and having a contrast around or above 5% to an operator into a visibility line on a user interface.

14. The system of claim 11, wherein the processor is configured to:
    obtain a contrast histogram of a plurality of pixels in the first region of interest at more than one distance; and
    select a plurality of bins of pixels having similar contrast histogram profiles.

15. The system of claim 11, wherein the processor is configured to:
    apply a Least Square method to calculate the visibility attenuation factor.

16. The system of claim 11 further including a digital imaging device.

17. The system of claim 11, wherein the digital imaging device is on board of a vehicle or machine.

18. The system of claim 11 further including a user interface configured to communicate to an operator of the determined visibility range.

19. The system of claim 18, wherein the user interface includes a visibility line to communicate to an operator of the determined visibility range.

20. The system of claim 11, wherein the processor is configured to select the first region of interest and the second region of interest.

* * * * *